(12) United States Patent
Kortenbach

(10) Patent No.: US 9,918,796 B2
(45) Date of Patent: Mar. 20, 2018

(54) ORTHOPAEDIC BONE DEPTH GAUGE AND METHOD

(71) Applicant: Biomet Manufacturing, LLC., Warsaw, IN (US)

(72) Inventor: Juergen Kortenbach, Miami Springs, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 1165 days.

(21) Appl. No.: 14/076,520

(22) Filed: Nov. 11, 2013

(65) Prior Publication Data

US 2015/0133944 A1 May 14, 2015

(51) Int. Cl.
*A61B 90/00* (2016.01)
*A61B 19/00* (2006.01)

(52) U.S. Cl.
CPC .............. *A61B 19/46* (2013.01); *A61B 90/06* (2016.02); *A61B 2090/061* (2016.02)

(58) Field of Classification Search
CPC ................ A61B 17/7092; A61B 90/06; A61B 2090/061; A61B 2090/062
USPC ............................ 606/102; 33/511, 512, 836
See application file for complete search history.

(56) References Cited

U.S. PATENT DOCUMENTS

| | | | | |
|---|---|---|---|---|
| 3,058,225 A * | 10/1962 | Ward | ..................... | A61C 19/04 33/513 |
| 4,033,043 A * | 7/1977 | Cunningham | ....... | A61B 5/1076 33/542 |
| 4,708,647 A * | 11/1987 | Pippin | .................. | A61C 19/043 433/32 |
| 5,013,318 A * | 5/1991 | Spranza, III | ......... | A61B 5/1076 33/512 |
| 6,729,037 B2 * | 5/2004 | White | ...................... | G01B 3/28 33/512 |
| 7,165,336 B2 * | 1/2007 | Kim | ...................... | A61B 5/1076 33/512 |
| 7,493,703 B2 * | 2/2009 | Kim | ...................... | A61B 5/1076 33/512 |
| 7,730,629 B2 * | 6/2010 | Kim | ...................... | A61B 5/1076 33/512 |
| 7,895,762 B2 * | 3/2011 | Kim | .......................... | G01B 3/28 33/512 |
| 8,512,349 B2 * | 8/2013 | Mengato | ................ | A61B 90/06 33/512 |
| 8,572,860 B2 * | 11/2013 | Fritzinger | .............. | A61B 90/06 33/512 |
| 8,728,088 B2 * | 5/2014 | LeBeau | .................. | A61B 17/88 606/102 |

* cited by examiner

*Primary Examiner* — Anu Ramana
(74) *Attorney, Agent, or Firm* — Schwegman Lundberg & Woessner, P.A.

(57) ABSTRACT

A bone depth gauge having a distal handle to which a tip is releasably connected. The tip is formed by photochemical machining to produce a tip and hook on the distal end with an approximate hexagonal cross section. The manufacturing costs of the tip are low enough to provide it in a one use package. A tubular element is releasably telescoped over the tip and handle to enable determination of the depth of a hole formed in a bone.

10 Claims, 2 Drawing Sheets

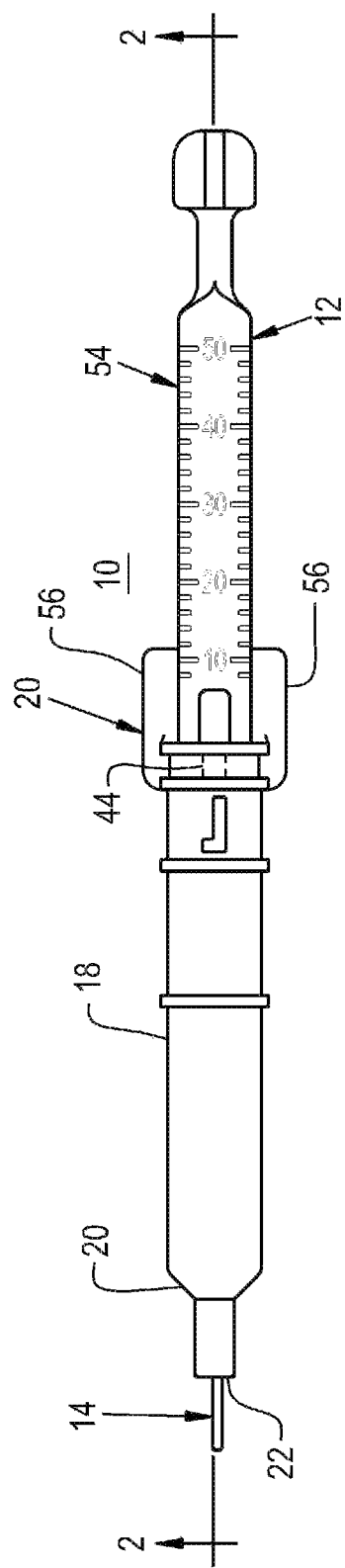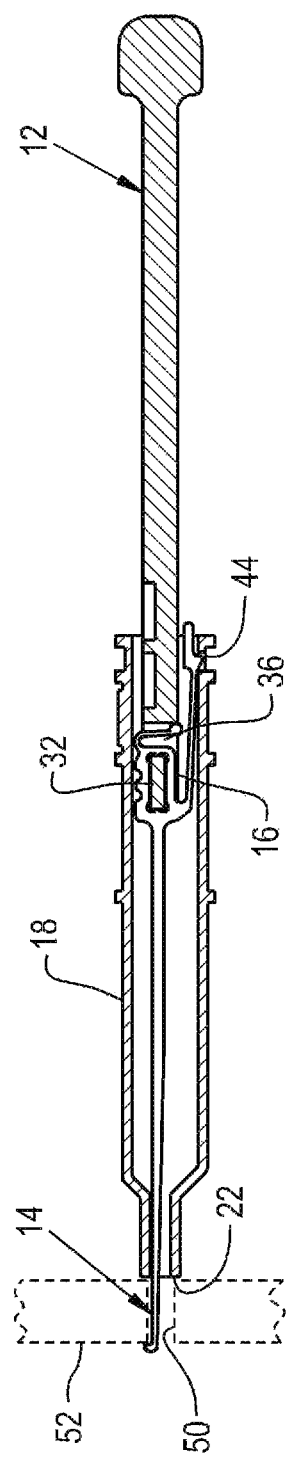

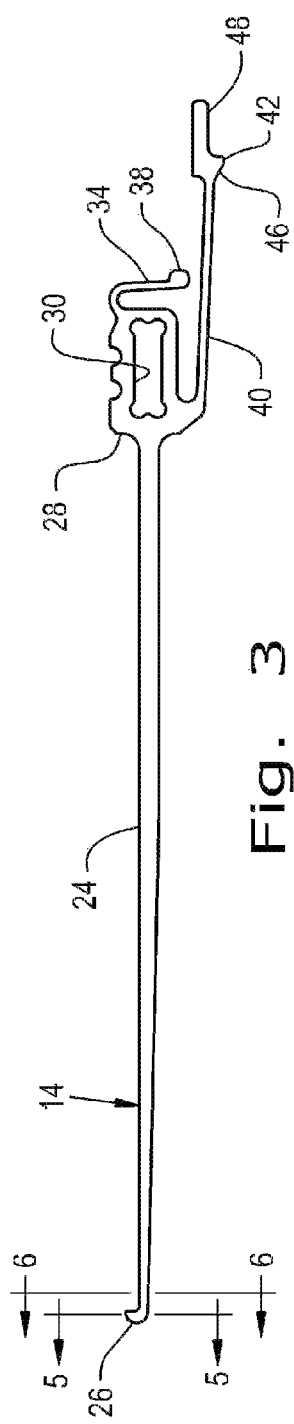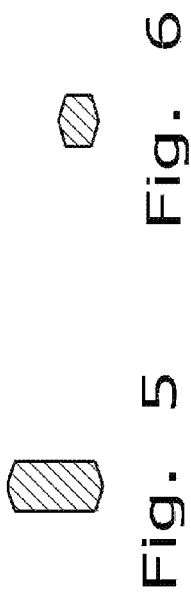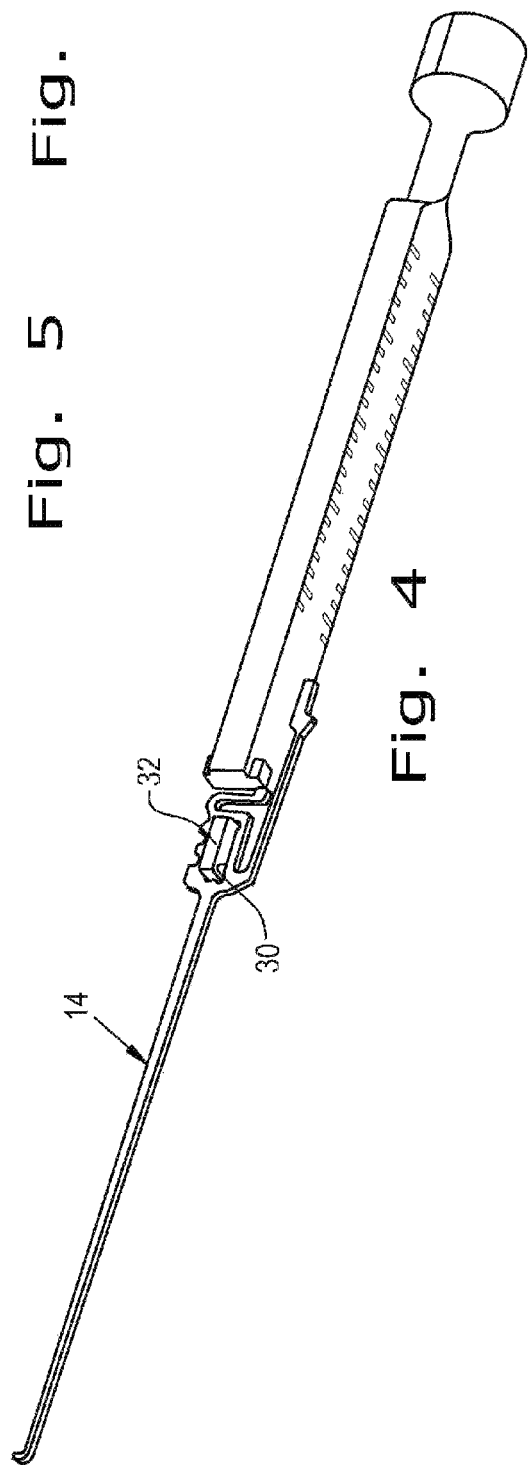

ORTHOPAEDIC BONE DEPTH GAUGE AND METHOD

BACKGROUND OF THE INVENTION

1. Field of the Invention

The present invention relates to the orthopaedic surgery art and more specifically to bone depth gauges.

2. Description of the Related Art

Installation of orthopaedic trauma reconstruction plates frequently require that holes be drilled through bones to allow the installation of screws that are used to restore the patient's natural anatomy. The depth of each hole must be measured so that the correct screw may be chosen to attach a support plate to the bone. Existing depth gauges used in re-sterilizable trays used for the operating room are usually far too expensive to discard after each use and are usually consigned to a hospital or surgical center. They are expected to be reused indefinitely.

Devices of this type, because of the long expected use, are typically machined, stainless steel or anodized aluminum with a stainless steel tip hook. This style of depth gauge has a hook that extends from the distal end of a tip and which is intended to hook on the opposite edge of a hole drilled through a bone to determine the bone depth. The tip is typically manufactured from a rod of steel and adds significantly to the cost of the assembly. The tip has a substantially round cross-section except for the distal end where there is a hook feature. The maximum width of the tip must be less than the diameter of the drilled hole so that it may be introduced into the drilled hole and hook the far edge of the hole. An outer housing telescoped over the tip is pushed forward and a mark on the housing indicates, on a graduated scale, the depth of the hole. Frequently, the depth gauge is removed from the bone and then read which adds the necessity for some kind of friction to hold the sliding members in position as it is withdrawn.

What is needed in the art, therefore, is an orthopaedic depth gauge in which the manufacturing costs of at least some of the components are reduced to the point that some of these may be made available as a single use item.

SUMMARY OF THE INVENTION

The present invention provides a cost effective bone depth gauge that may be available in a single use form.

In one form, the invention is an orthopaedic bone depth gauge with a proximal handle and an elongated metal tip releasably connected to the handle with the tip having a hook on its distal end for engaging the opposite face of a bone through which a hole has been formed. The tip is formed by photo chemical machining A tubular element has a distal end telescoped over the tip and a proximal end telescoped over the handle with the tubular element being releasably retained by the tip. The tubular element and handle cooperate to provide indicia for measuring the bone depth when the hook of the tip engages the opposite face of the bone and the distal end of the tubular element engages the near face of the bone through which the hole has been formed.

In another form, the invention is a tip for use with a bone depth gauge having a proximal handle. The tip includes a thin metal element having an elongated shaft and an integral hook at the distal end of the shaft, the element having a configuration integrally connected to the shaft at the proximal end thereof for releasable connection to the handle with the thin metal element being formed by photo chemical machining.

In still another form, the invention is a method of manufacturing a tip for use with an orthpaedic depth gauge having a proximal handle and a tubular element telescoped over the handle and tip to measure bone depth. The method includes applying a photo resistant layer having a negative pattern of the tip configuration onto a sheet-like element and exposing the photo resist layer to light to harden the negative patterns. The non-hardened photo resistant portions are removed chemically and then the sheet-like element is chemically etched to remove all but the portion covered by the negative. Subsequently the photo resist material is chemically stripped from the sheet-like element to produce a final shape.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a longitudinal side view of an orthopaedic depth gauge embodying the present invention;

FIG. 2 is a longitudinal section view taken on lines 2-2 of FIG. 1;

FIG. 3 is a side view of a tip used in the depth gauge of FIGS. 1 and 2;

FIG. 4 is a perspective view of the depth gauge tip and handle with a tubular element removed; and, FIGS. 5 and 6 show cross sections of the depth gauge tip of FIG. 3, taken on lines 5-5 and 6-6 of FIG. 3.

Corresponding reference characters indicate corresponding parts throughout the several views. The exemplification set out herein illustrates one embodiment of the invention and such exemplification is not to be construed as limiting the scope of the invention in any manner.

DETAILED DESCRIPTION OF THE INVENTION

FIG. 1 shows an orthopaedic bone depth gauge 10 which includes a proximal handle 12 providing a mounting for a tip 14 on the distal end 16 of handle 12. A tubular element 18 is telescoped over the assembly and has a proximal end 20 over handle 12 and a distal end 22 over tip 14.

Referring now to FIG. 3, tip 14 is made of thin metal sheet up to around 1 mm in thickness, preferably up to 1.07 mm thickness). The configuration illustrated in FIG. 3 is a final configuration before assembly with the handle 12 and tubular element 18. Tip 14 has an elongated shaft 24 terminating in a hook 26 at its distal end. At the proximal end 28 there is a window 30 sized and configured to be received over a post 32 integral with handle 12. A tab 34 is coplanar with the tip 14 and has a flexible section configured to be received in a notch 36 on handle 12. A tab 38, integral with tab 34, permits an operator to depress tab 34 sufficiently to clear notch 36 and remove tip 14 laterally from post 32. A friction arm 40 is also integral with the proximal end 28 and extends longitudinally in a slightly radially outward direction and has a tip 42 for engaging the inner surface of tubular element 18 thus providing friction against movement and in addition to provide a limit to the displacement of tubular element 18 away from the proximal end of handle 12 by abutting a window feature 44 on the proximal end of tubular element 18 that tip 42 flexes into under spring force. Tip 42 has a ramp feature 46 enabling the tubular element 18 to be slipped over arm 40 during assembly. A tab 48 extends sufficiently beyond the distal end of tubular element 18 when window 44 abuts tip 42 to enable the arm 40 to be displaced radially inward and permit disassembly of the unit.

FIG. 4 shows the interconnection between the tip 14 and handle 12 and illustrates the post 32 over which the window 30 is moved and the notch in the handle 12 for receiving tab 34.

Referring now to FIG. 2 the shaft 24 of tip 14 is introduced into a hole 50 that has been drilled through a bone 52, both shown by dashed lines. The hook 26 is engaged with the opposite face of the bone 52 and the tubular element 18 is displaced to the left until its distal end 22 abuts the near face of the bone 52. A graduated scale 54 on handle 12 lines up with the proximal end 20 of tubular element 18 to indicate the depth of the hole 50, typically in millimeters. Tabs 56 extending from tubular element 18 may have marks on them for easy determination of the bone size. This enables the proper screw selection, taking into account the thickness of any support device for the particular fixture. Tubular element 18 and handle 54 may be formed from widely available surgical plastic material for example (Radel) plastic. This plastic is re-sterilizable and reusable.

In accordance with another aspect of the present invention, the tip 14 is formed by photo chemical machining This process enables significant reductions in manufacturing costs and reduces the unit cost of tip 14 to the point where it is economically feasible to provide the tip 14 in a one use package. The process begins with providing a sheet of metallic material, typically stainless steel used in surgery. A photo sensitive sheet with an adhesive back is rolled preferably on both sides of the sheet and then a machine loads a photo negative of the material of the ultimate configuration in a glass press and this is done on both sides. Subsequently, both sides are exposed to a light source such as ultraviolet to harden the exposed portion of the tip configuration, namely what is contained outside of the negative. The material that has not been hardened is then stripped by a bath which immerses the sides in a chemical that strips the exposed areas away, leaving the configuration of the part as shown in FIG. 3. The sheet material is then etched in a system which uses high pressure acid traversing the sheet to eat away at the portions of the material not covered by the photo resist. Typically, on each side, the etching extends to about 60% of the thickness of the material. When it is done to opposite sides, it cuts through the material. One of the features of the photo chemical process is that a portion of the chemical etching slips underneath the photo resist so that the end configuration is a semi-hexagonal shape as shown in FIGS. 5 and 6. This is particularly advantageous when the tip is used for entry through the hole 50 since it more closely approximates a round configuration. Subsequent to the photo etching process, the photo resist is stripped from the sheet and then the entire finished part is subjected to a brief acid etching, referred to as a post etch, to remove sharp edges that may be a cutting hazard.

The net result of the process used in the formation of tip 14 enables significant reductions in the cost of manufacturing the tip 14. In fact, the manufacturing cost is reduced sufficiently so that the tip 14 may be provided in a one use system in which the tip is prepackaged and then subjected to gamma rays for complete sterilization. Thus, the user has the option of either re-sterilizing the tip or using the tip 14 in a one use system. In either application, the tip 14 has significant benefits in terms of ease of disassembly and a simplified structure that provides retention and friction characteristics for the device.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic bone depth gauge, comprising:
    a proximal handle having a graduated scale;
    an elongated metal tip releasably connected to said handle, said tip having a hook on its distal end for engaging the opposite face of a bone through which a hole has been formed, said tip being formed by photochemical machining; and,
    a tubular element having a distal end telescoped over said tip and a proximal end telescoped over said handle, said tubular element being releasably retained by said tip, said proximal end of said tubular element positionable along the graduated scale to indicate a bone depth when the hook of said tip engages the opposite face of the bone and the distal end of said tubular element engages the near face of the bone through which the hole has been formed.

2. The bone depth gauge of claim 1, wherein the tip is sterilized during manufacture to make it disposable.

3. The bone depth gauge of claim 1, wherein the tip has a thickness of up to 1.07 mm.

4. The bone depth gauge of claim 3, wherein the photo chemical machining produces an approximately hexagonal shaped cross-sectional shape to said tip.

5. The bone depth gauge of claim 4, wherein the tip is photo chemically etched (post etched) subsequent to formation to remove sharp edges therefrom.

6. The bone depth gauge of claim 1, wherein the handle has a protrusion in its distal end and the tip has a window in its proximal end for being supported by the distal end of the handle, said tip further including an integral lock tab yieldable to permit the tip to be disengaged from the distal end of the handle.

7. The bone depth gauge of claim 1, wherein the tubular element has a window in the tubular element on the proximal end thereof and the proximal end of the tip has a tab yieldably urged radially outward against the tubular element to provide friction and to retain the tubular element over the tip by receiving the tab within the window, said tab being flexible radially inward with respect to an outer surface of the tubular element to permit disengagement of the tubular element from the tip.

8. The bone depth gauge of claim 7, wherein the tip further includes a tab extending beyond the distal end of the tubular element for providing an operator detent to remove the tubular element.

9. The bone depth gauge of claim 1, wherein said tip is formed as a thin metal element having an elongated shaft and the hook formed integrally at the distal end of said shaft.

10. The bone depth gauge of claim 9, wherein the tubular element has a window at the proximal end thereof, said tip including a tab yieldably urged radially outward to engage the interior of the tubular element within the window of the tubular element, the engagement frictionally retaining the tubular element over the tip, said tab being flexible radially inward to permit disengagement of the tubular element from the tip.

* * * * *